(12) United States Patent
Dalton et al.

(10) Patent No.: US 10,004,882 B2
(45) Date of Patent: Jun. 26, 2018

(54) IMPLANTABLE SYSTEM FOR COLLECTION AND SUPPLY OF INTERSTITIAL FLUID

(71) Applicants: Michael J. Dalton, Evanston, IL (US); Natan A. Pheil, Chicago, IL (US); Jordan M. Dalton, Libertyville, IL (US)

(72) Inventors: Michael J. Dalton, Evanston, IL (US); Natan A. Pheil, Chicago, IL (US); Jordan M. Dalton, Libertyville, IL (US)

( * ) Notice: Subject to any disclaimer, the term of this patent is extended or adjusted under 35 U.S.C. 154(b) by 495 days.

(21) Appl. No.: 14/662,986

(22) Filed: Mar. 19, 2015

(65) Prior Publication Data
US 2015/0190620 A1    Jul. 9, 2015

Related U.S. Application Data

(63) Continuation-in-part of application No. 14/182,418, filed on Feb. 18, 2014.
(Continued)

(51) Int. Cl.
| A61M 1/00 | (2006.01) |
|---|---|
| A61M 27/00 | (2006.01) |
| A61M 39/24 | (2006.01) |
| A61F 2/02 | (2006.01) |
| A61K 35/39 | (2015.01) |
| A61K 35/12 | (2015.01) |
| A61M 5/14 | (2006.01) |
| A61M 5/172 | (2006.01) |
| A61M 5/142 | (2006.01) |

(52) U.S. Cl.
CPC .......... *A61M 27/002* (2013.01); *A61F 2/022* (2013.01); *A61K 35/12* (2013.01); *A61K 35/39* (2013.01); *A61M 5/1407* (2013.01); *A61M 5/14276* (2013.01); *A61M 5/1723* (2013.01); *A61M 39/24* (2013.01); *A61M 2005/14208* (2013.01); *A61M 2202/09* (2013.01)

(58) Field of Classification Search
CPC .......... A61M 27/002; A61M 2205/75; A61M 5/1407; A61M 5/14276; A61M 5/1723; A61M 39/24; A61F 2/022; A61K 35/12; A61K 35/39

See application file for complete search history.

(56) References Cited

U.S. PATENT DOCUMENTS

| 3,738,365 A * | 6/1973 | Schulte | ............... A61M 25/005 |
|---|---|---|---|
| | | | 604/523 |
| 3,750,194 A | 8/1973 | Summers | |

(Continued)

OTHER PUBLICATIONS

STIC Search, Sep. 1, 2015, 14 pages.

(Continued)

*Primary Examiner* — Ariana Zimbouski
(74) *Attorney, Agent, or Firm* — Klintworth & Rozenblat IP LLP

(57) ABSTRACT

A system for redistributing interstitial fluid within a mammal is disclosed. The system comprises an implantable accumulation chamber, a confined flow passageway such as a catheter in communication with the accumulation chamber, and a liquid transfer pump for dispensing accumulated interstitial fluid from the accumulation chamber to a predetermined body site via the confined flow passageway.

18 Claims, 5 Drawing Sheets

Related U.S. Application Data

(60) Provisional application No. 61/766,111, filed on Feb. 18, 2013, provisional application No. 61/955,307, filed on Mar. 19, 2014.

(56) References Cited

U.S. PATENT DOCUMENTS

| | | |
|---|---|---|
| 6,511,473 B2 | 1/2003 | Bartha et al. |
| 7,043,295 B2 | 5/2006 | Starkebaum |
| 7,637,897 B2 | 12/2009 | Ginggen |
| 8,702,684 B2 | 4/2014 | Bodor et al. |
| 2008/0039792 A1* | 2/2008 | Meng .................. A61K 9/0024 604/114 |
| 2009/0318844 A1* | 12/2009 | Burnett ............... A61M 27/002 604/9 |
| 2012/0172782 A1* | 7/2012 | Thompson .......... A61B 17/1114 604/8 |
| 2013/0289540 A1 | 10/2013 | Zeltser et al. |
| 2014/0155806 A1* | 6/2014 | Cheng ................. A61M 27/002 604/9 |

OTHER PUBLICATIONS

Non-Final Office Action for U.S. Appl. No. 14/182,418, dated Oct. 26, 2015, 21 pages.

Final Office Action for U.S. Appl. No. 14/182,418, dated Mar. 15, 2016, 22 pages.

Non-Final Office Action for U.S. Appl. No. 14/182,418, dated Oct. 26, 2016, 27 pages.

Final Office Action for U.S. Appl. No. 14/182,418, dated Jun. 29, 2017, 34 pages.

* cited by examiner

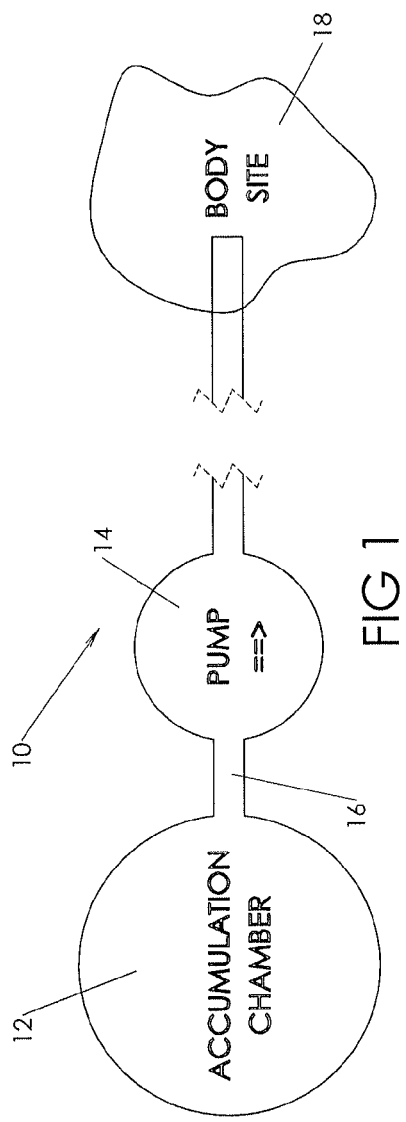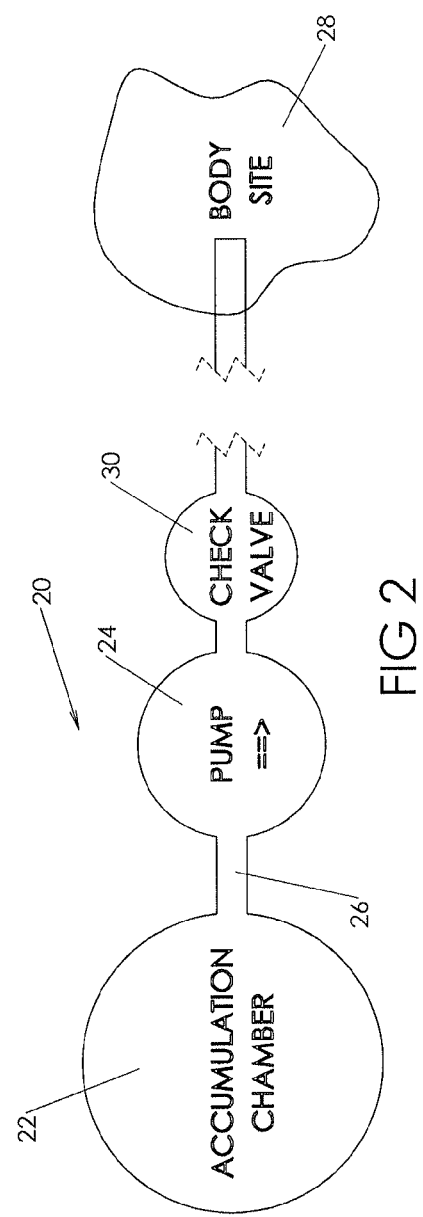

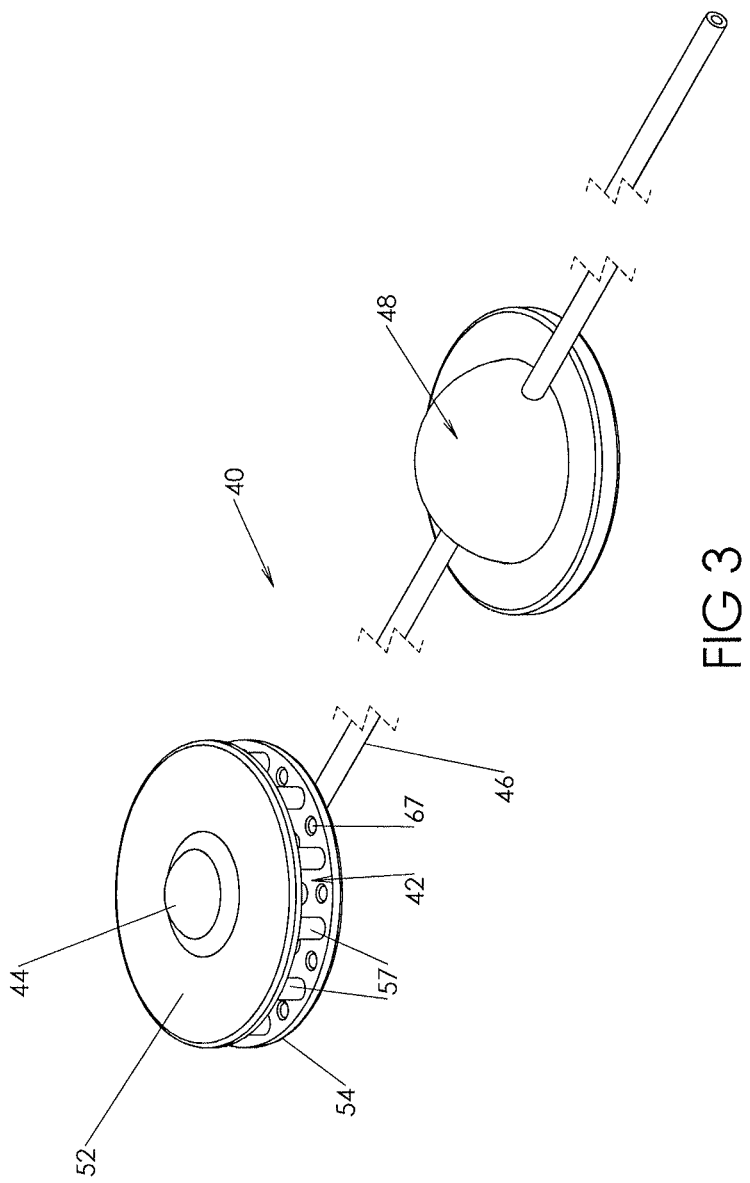

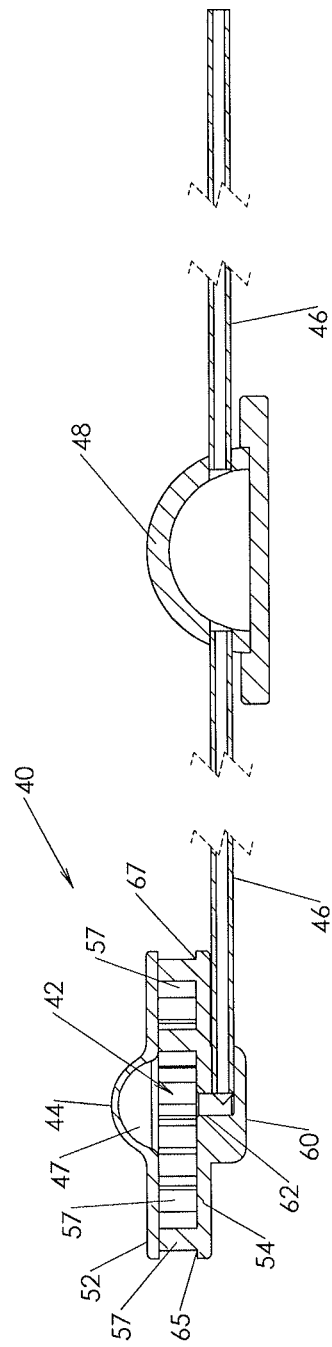

IMPLANTABLE SYSTEM FOR COLLECTION AND SUPPLY OF INTERSTITIAL FLUID

CROSS-REFERENCE TO RELATED APPLICATIONS

This application is a continuation-in-part of U.S. patent application Ser. No. 14/182,418, filed on Feb. 18, 2014, which claims benefit of U.S. Provisional Patent Application No. 61/766,111, filed on Feb. 18, 2013. This application also claims benefit of U.S. Provisional Patent Application No. 61/955,307, filed on Mar. 19, 2014. Said applications are incorporated herein by reference in their entireties.

FIELD OF INVENTION

This application relates to collection and distribution of interstitial fluid for use in medical or veterinary therapy and research.

BACKGROUND OF THE INVENTION

Interstitial fluid is found in the interstitial spaces of a multicellular animal. It is the main component of extracellular fluid and a source of nutrients for the cells. Interstitial fluid contains glucose, salt, fatty acids, minerals such as calcium, magnesium and potassium, as well as oxygen and other components essential to the survival of cells. Interstitial fluid receives its components via capillaries by means of diffusion.

While significant research effort has been expended regarding the use of interstitial fluid as a biomarker for cancer research and diagnosis, research pertaining to use of interstitial fluid for treatment of disease or damaged tissue appears to be lacking. It has now been found that autologous interstitial fluid can be effectively collected and utilized to provide essential sustenance to preselected target cells at a body site remote from the collection site.

SUMMARY OF INVENTION

Autologous interstitial fluid is collected at a collection site within the patient and supplied to a remote body site. A pool of interstitial fluid is accumulated at a first body site within a mammal and at least a portion thereof is dispensed at a second body site remote from the first body site.

In particular, an implantable, biocompatible system for distributing or supplying interstitial fluid from the collection site to a remote body site of the patient comprises a hollow accumulation chamber, a confined flow passageway in liquid flow communication with the hollow accumulation chamber, and a liquid transfer pump operably associated with the accumulation chamber to dispense interstitial fluid therefrom to the remote body site through the confined flow passageway.

The hollow accumulation chamber is defined by an external or top plate, and an internal or bottom plate juxtaposed relative to the external or top plate and spaced therefrom by a plurality of spacer members or posts. A flexible dome is integral with the external or top plate, and can serve as a pump to dispense interstitial fluid from the accumulation chamber.

BRIEF DESCRIPTION OF DRAWINGS

In the drawings,

FIG. 1 is a schematic representation of an interstitial fluid delivery system comprising an interstitial fluid collection chamber in communication with a confined flow passageway and having a liquid transfer pump in the confined flow passageway;

FIG. 2 is a schematic representation of an interstitial fluid delivery system comprising an interstitial fluid collection chamber in communication with a confined flow passageway and having a unidirectional check-valve in the confined flow passageway;

FIG. 3 is a perspective view of an interstitial fluid dispensing system having a domed interstitial fluid collection chamber and a confined flow passageway in communication therewith;

FIG. 4 is a sectional elevation of the interstitial fluid dispensing system shown in FIG. 3;

DESCRIPTION OF PREFERRED EMBODIMENTS

Figure 5:
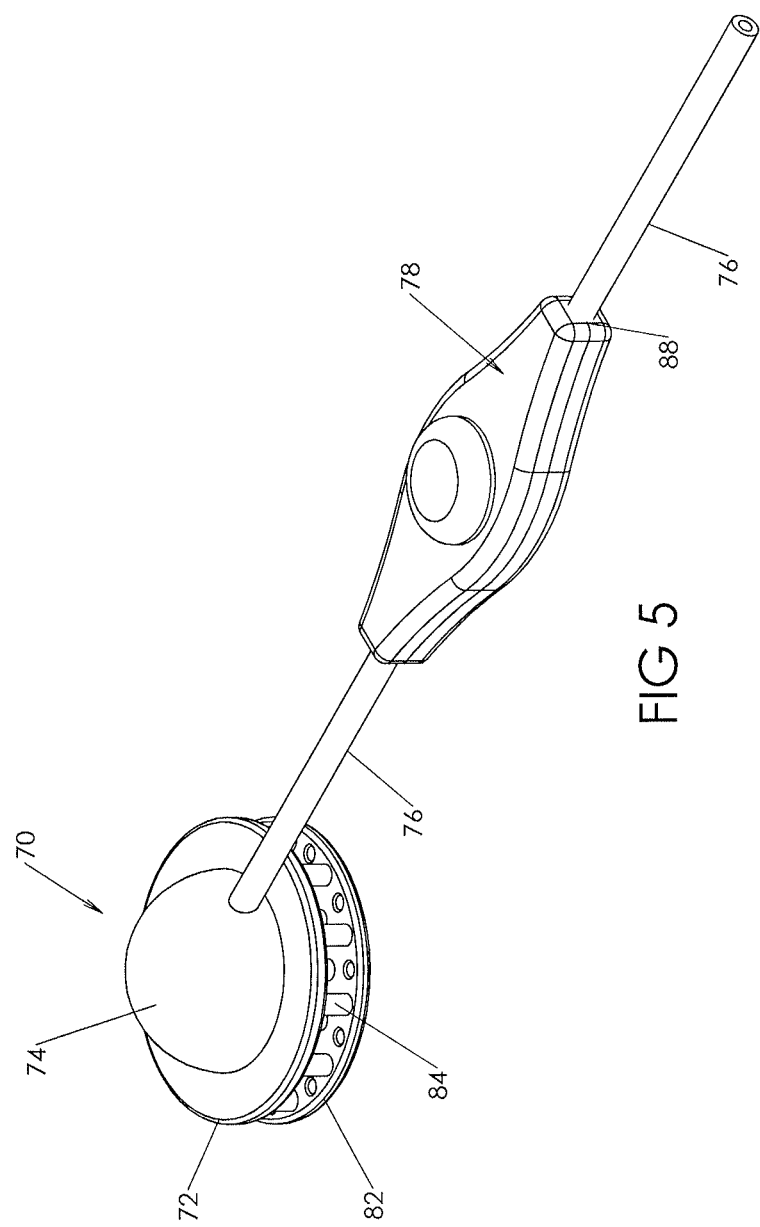
FIG. 5 is a perspective view of an alternate embodiment of an interstitial fluid dispensing system embodying the present invention.

Referring to the drawings, FIG. 1 schematically illustrates an implantable, biocompatible system embodying the invention. System 10 comprises an implantable accumulation chamber 12, liquid transfer pump 14, and a confined flow passageway such as outlet catheter 16 which is in liquid flow communication with accumulation chamber 12. Outlet catheter 16 dispenses interstitial fluid collected in accumulation chamber 12 at a preselected body site 18 which is populated by cells in need of additional nutrients. Body site 18 can be a lesion such as damaged tissue, an open wound, and the like, or transplanted cells such as the Islets of Langerhans for treatment of diabetes, autologous and allogeneic pluripotent stem cells, and the like.

Transport of interstitial fluid from accumulation chamber 12 to body site 18 is facilitated by liquid transfer pump 14. Various types of pumps can be utilized for this purpose, such as a peristaltic pump, a gear pump, a piston-type metering pump, an elastomeric dome integral with a housing portion of accumulation chamber 12 and in communication with outflow catheter 16. In certain applications a programmable, computer controlled electromechanical pump may be used, as in the case of insulin delivery where various flow rates are required during a normal day. Feedback from a sensor either integral with the pump or situated in a predetermined remote location may be used to regulate the pumping rate, which may be continuous or intermittent.

FIG. 2 shows an alternate embodiment of a system embodying the invention. In particular, system 20 comprises accumulation chamber 22, liquid transfer pump 24, catheter 26 in liquid flow communication with accumulation chamber 22, and unidirectional flow checkvalve 30 downstream from liquid transfer pump 24 and associated with the confined flow passageway defined by catheter 26. Incorporation of check-valve 30 into the system is advantageous when pump 24 is an elastomeric dome integral with a housing portion of accumulation chamber 22.

The relative locations of liquid transfer pump 24 and check-valve 30 can be interchanged, if desired, for a particular application. In some instances the check-valve can be situated at an exit port of accumulation chamber 22.

FIGS. 3 and 4 show an interstitial fluid distribution system having a dispensing pump integral with an accumulation chamber. System 40 includes accumulation chamber 42 with flexible dome 44, pump 48 for liquid transfer, and catheter 46 in liquid flow communication with accumulation chamber 42.

Accumulation chamber 42 is defined by chamber housing external or top plate 52, flexible dome 44 and chamber housing internal or bottom plate 54 which is juxtaposed relative to top plate 52 and spaced therefrom. Top plate 52 and bottom plate 54 are maintained in a spaced relationship relative to one another by a plurality of posts 57 integral with top plate 52 and bottom plate 54.

The space between the top plate 52, including dome 44, and the bottom plate 54 is open and is determined by the volume of the interstitial fluid that needs to be accumulated. Posts 57 are situated around the periphery of accumulation chamber 42 and create a tortuous path for tissue ingrowth while preventing tissue ingrowth from totally encapsulating accumulation chamber 42. The spacing between the plates 52 and 54 and the placement of the posts 57 are predetermined to minimize tissue from growing over the plates and totally occluding the plates. The shape of the accumulation chamber 42 is selected to conform to the contour of the body and of a thickness that can be tolerated in the intended subcutaneous environment. Pump 48 conveys interstitial fluid collected in accumulation chamber 42 to a preselected body site via catheter 46.

Top plate 52 and bottom plate 54 can be fabricated of pliable medical grade silicone rubber, e.g., certified USP Class V or Class VI materials, or any other biocompatible elastomeric material or metal such as stainless steel. The open proximal end of the outflow catheter such as catheter 16 is placed in the open center portion of accumulation chamber 42, and is protected from invading tissue by posts 57 that create a tortuous path for tissue invasion. The spacing of the top and bottom plates from one another is such that the surrounding tissue does not grow across the gap created between the top and bottom plates The spacing between plates 52 and 54 preferably is in the range of about 1.5 mm to about 5 mm, more preferably about 3 mm. The center portion of the accumulation chamber remains open to allow for fluid accumulation. The posts may be medical grade silicone rubber, metal or a biocompatible elastomeric mesh or screen. The material of construction and chamber size are selected to prevent tissue and capillaries from invading the center of the chamber, thereby occluding the outlet catheter.

Proximal end of catheter 46 terminates in an open, hollow bell-shaped catheter connection 60 which is in communication with the interior of accumulation chamber 42 via aperture 62 defined in bottom plate 54 and together with bell-shaped catheter connection 60 defines a drain for accumulation chamber 40.

Dome 44 is an elastomeric half-shell made of silicone rubber, integral with top plate 52 and surrounds aperture 47 defined in top plate 52. Depression of half-shell can assist pump 48 in expelling accumulated interstitial fluid from accumulation chamber 40 into catheter 46 via the drain defined by aperture 62, or can aid in priming pump 48.

Peripheral apertures such as apertures 65 and 67 in bottom plate 54 are provided for securing accumulation chamber 40 to adjacent tissue with sutures and the like.

An illustrative round accumulation chamber has an external diameter of about 47 millimeters, and top plate and bottom plate thickness of about 1.5 millimeters. The posts have an outside diameter of about 2.5 millimeters, and the spacing between the top plate and the bottom plate is about 3.5 millimeters.

Figure 6:
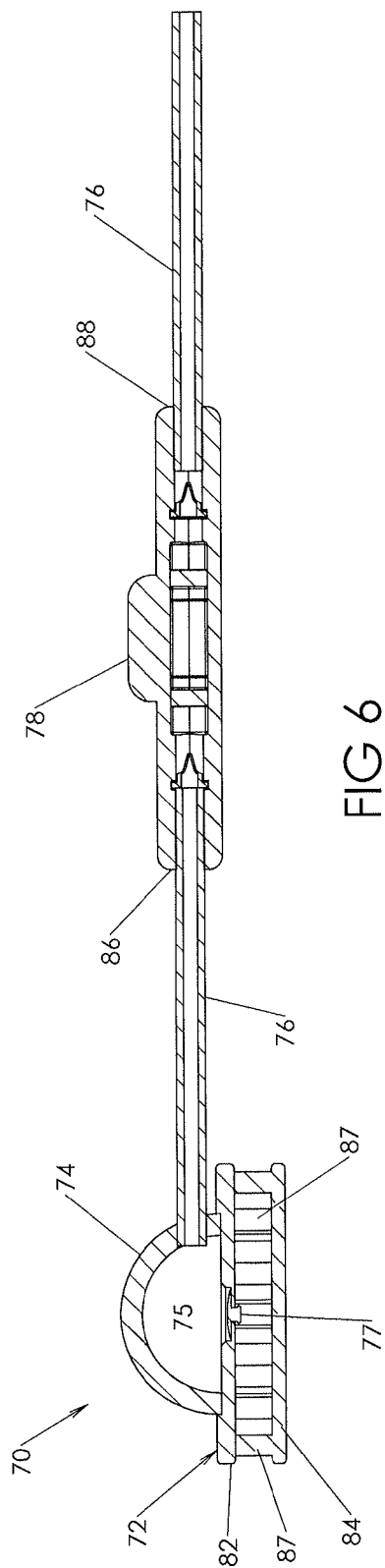
FIG. 6 is a sectional elevation of the system shown in FIG. 5.

FIGS. 5 and 6 show an alternate embodiment of an interstitial fluid distribution system. System 70 includes accumulation chamber 72 with flexible dome 74, catheter 76 and receptacle 78 suitable for housing a live cell culture to be nourished by the interstitial fluid.

Accumulation chamber 72 comprises top plate 82, dome 74 integral with top plate 82, bottom plate 84, and a plurality of posts 87. The overall configuration of accumulation chamber 72 is similar to that of accumulation chamber 42. In this particular embodiment, dome 74 defines a space that receives an aliquot of interstitial fluid that is dispensed to receptacle 78 when dome 74 is collapsed by applied physical pressure or by an applied negative pressure when a pump is provided between accumulation chamber 72 and receptacle 78. Catheter 76 is in liquid flow communication with space 75. Check-valve 77 in top plate 82 prevents backflow of interstitial fluid when dome 74 is collapsed.

Receptacle 78 is provided with at least one inlet port 86 and at least one outlet port 88. More than one inlet port can be provided in receptacle 78, if desired, so that interstitial fluid from more than one accumulation chamber can be supplied to receptacle 78. In a like manner, more than one outlet port can be provided in receptacle 78, so that the interstitial fluid received therein can be distributed to more than one predetermined body site.

The overall contour of the receptacle can vary depending on the implant site. The receptacle is made of a biocompatible material and can be a solid housing, a porous housing, a liquid permeable sac, and the like. If the receptacle is made of a porous material and a colony of live cells is contained therein, the material porosity is such as to prevent cells from leaving the receptacle. A preferred material porosity is in the range of about 10 microns to about 200 microns.

The receptacle can serve as a containment space for a colony of live cells that receive nourishment from surrounding interstitial fluid. The receptacle can receive interstitial fluid from several implanted accumulation chambers, if desired, by providing appropriate liquid flow passageways therebetween.

For cell-based therapies, such as hormone replacement therapies, colonies of live cells, such as human islet cells secreting insulin, porcine islet cells secreting insulin, ovarian cells secreting sex hormones, thyroid epithelial cells secreting thyroxine and triiodothyronine, and the like, are contained within the receptacle and surrounded by (or bathed in) the interstitial fluid received from one or more accumulation chambers.

The interstitial fluid collected in the accumulation chamber preferably is free from debris and defense mechanisms of the host. The preferred shape of the accumulation chamber is circular or round; however, any biomedically appropriate shape compatible with the selected implantation site can be utilized.

The accumulated interstitial fluid is transported to a desired location by an electromechanical or mechanical pump connected to or fixed to the accumulation chamber. A benefit of the present invention is that the interstitial fluid, naturally occurring in the body, can be collected and then conveyed to any location in need of nutrients and oxygen.

EXAMPLE

Interstitial fluid delivery system consisting of an accumulation chamber and a catheter in liquid flow communication therewith as shown in FIGS. 5 and 6 was implanted in two male Lewis rats. The interstitial fluid collected in the accumulation chamber was dispensed into an implanted receptacle (an isolation receptacle used for maintenance of transplanted cells) using a mechanical pump.

The Lewis rats were maintained for 50 days. Interstitial fluid was sampled from the accumulation chamber as well as from the receptacle and analyzed for nutrients and oxygen concentration.

No complications were observed as a result of the implant procedure. Post-operative healing and recovery were normal. The rats tolerated the implant well.

The collected interstitial fluid was serosanguineous for at least 21 days; red blood cell containment appeared to decrease with passage of time, however. The collection protocol is shown in Table 1, below.

TABLE 1

Collection Protocol

| Rat ID | Day +6 Amount, ml AC | Day +6 Amount, ml RCPT | Day +6 Fluid Appearance | Day +18 Amount, ml AC | Day +18 Amount, ml RCPT | Day +18 Fluid Appearance | Day +21 Amount, ml AC | Day +21 Amount, ml RCPT | Day +21 Fluid Appearance |
|---|---|---|---|---|---|---|---|---|---|
| A161 | 1.2 | N/C | SSNG | 3.0 | 1.0 | SSNG | 1.5 | 1.4 | SSNG |
| A162 | 1.0 | N/C | SSNG | 3.0 | 2.0 | SSNG | 2.5 | 1.2 | SSNG |

AC—accumulation chamber
RCPT—receptacle
SSNG—serosanguineous

Aliquots of interstitial fluid from the accumulation chamber and the receptacle were analyzed for nutrient, oxygen and $CO_2$ content using i-STAT Portable Clinical Analyzer in conjunction with EG7+ cartridge. The obtained results are shown in Table 2, below.

TABLE 2

Components of Interstitial Fluid

| Component | Day +6 AC A161 | Day +6 AC A162 | Day +18 AC A161 | Day +18 RCPT A161 | Day +18 AC A162 | Day +18 RCPT A162 | Day +21 AC A161 | Day +21 RCPT A161 | Day +21 AC A162 | Day +21 RCPT A162 | Reference Range* Arterial | Reference Range* Venous |
|---|---|---|---|---|---|---|---|---|---|---|---|---|
| Sodium (Na) mmol/L | 143 | 143 | 141 | 141 | 143 | 140 | 142 | 141 | 143 | 141 | 138-146 | 138-146 |
| Potassium (K) mmol/L | 4.4 | 4.3 | 4.6 | 4.4 | 4.5 | 5.2 | 4.4 | 4.6 | 4.4 | 4.9 | 3.5-4.9 | 3.5-4.9 |
| Ionized Calcium (iCa) mmol/L | 5.7 | 5.4 | 5.3 | 4.8 | 5.6 | 4.9 | 5.2 | 4.9 | 5.5 | 4.9 | 4.5-5.3 | 4.5-5.3 |
| Hematocrit (Hct) PCV % | <10% | <10% | <10% | <10% | <10% | <10% | <10% | <10% | <10% | <10% | 38-51% | 38-51% |
| Hemoglobin (Hgb) g/dL | ◇ | ◇ | ◇ | ◇ | ◇ | ◇ | ◇ | ◇ | ◇ | ◇ | 12-17 | 12-17 |
| pH | 7.278 | 7.296 | 7.395 | 7.398 | 7.328 | 7.201 | 7.487 | 7.251 | 7.293 | 7.196 | 7.35-7.45 | 7.31-7.41 |
| $PCO_2$ mmHg | 62.9 | 57.8 | 42.5 | 31.3 | 54.6 | 54.8 | 36.9 | 45.8 | 61.9 | 48.7 | 35-45 | 41-51 |
| $PO_2$ mmHg | 51 | 41 | 89 | 111 | 110 | 110 | 119 | 90 | 64 | 83 | 80-105 | |
| Base Excess (BE) mmol/L | 3 | 2 | 1 | -6 | 3 | -7 | 5 | -7 | 3 | -9 | (-2)-(+3) | (-2)-(+3) |
| $HCO_3$ mmol/L | 29.5 | 28.1 | 26 | 19.3 | 26.7 | 21.4 | 27.9 | 20.1 | 30 | 18.9 | 22-26 | 23-28 |
| $TCO_2$ mmol/L | 31 | 30 | 27 | 20 | 30 | 23 | 29 | 22 | 32 | 20 | 23-27 | 24-29 |
| $sO_2$% | 79 | 69 | 97 | 93 | 98 | 97 | 99 | 95 | 89 | 93 | 95-98% | |

*Obtained from arterial and venous blood vessels of rat

Glucose levels of the interstitial fluid were measured using an i-STAT G-cartridge. The observed results are shown in Table 3, below.

TABLE 3

Glucose Level of Interstitial Fluid

POC Blood Glucose, mg/dl

| Rat ID | Day +6 AC | Day +6 TS | Day +18 AC | Day +18 RCPT | Day +18 TS | Day +21 AC | Day +21 RCPT | Day +21 TS |
|---|---|---|---|---|---|---|---|---|
| A161 | 164, 171 | 150, 159 | 75 | <20 | 160 | 91 | <20 | 154 |
| A162 | 164, 185 | 175, 176 | 108 | <20 | 143 | 110 | <20 | 134 |

TS—tail stick

As can be seen from the above data, the interstitial fluid can adequately supply needed nutrient and oxygen for cell survival. The measured component values were within the range of the reference values from arterial and venous blood vessels of the animal.

Additionally, it was determined that the implanted system remained patent during the entire 50-day test period and continued to supply an adequate amount of interstitial fluid.

The foregoing specification and the drawings are illustrative, and are not intended to be limiting. Still other variations within the spirit and scope of the present invention are possible and will readily present themselves to one skilled in the art.

The invention claimed is:

1. An implantable, biocompatible system for distributing interstitial fluid from a collection site to a remote body site of a patient which comprises;
    a hollow accumulation chamber comprising a plurality of posts forming a tortuous path for tissue to grow into and having spacing between the plurality of posts to prevent the tissue from blocking the hollow accumulation chamber while allowing the interstitial fluid to flow into the hollow accumulation chamber between the plurality of posts;
    a confined flow passageway in liquid flow communication with the hollow accumulation chamber; and
    a liquid transfer pump operably associated with the hollow accumulation chamber for dispensing interstitial fluid from the hollow accumulation chamber to the remote body site through the confined flow passageway.
2. The implantable, biocompatible system in accordance with claim 1 wherein the liquid transfer pump is situated in the confined flow passageway.

3. The implantable, biocompatible system in accordance with claim 1 wherein the liquid transfer pump is a flexible dome integral with the hollow accumulation chamber.

4. The implantable, biocompatible system in accordance with claim 3 wherein a unidirectional check-valve is present in the confined flow passageway preventing return flow of dispensed interstitial fluid.

5. The implantable, biocompatible system in accordance with claim 1 wherein the hollow accumulation chamber comprises first and second opposed plates spaced apart from one another, the plurality of posts connected to and extending between the first and second opposed plates, the first plate connected to a flexible dome.

6. The implantable, biocompatible system in accordance with claim 1 wherein the liquid transfer pump is integral with the hollow accumulation chamber.

7. The implantable, biocompatible system in accordance with claim 6 wherein the liquid transfer pump is a flexible dome integral with the hollow accumulation chamber.

8. The implantable, biocompatible system in accordance with claim 7 wherein the confined flow passageway is connected to the flexible dome.

9. The implantable, biocompatible system in accordance with claim 5 further comprising a check-valve disposed in the first opposed plate, the liquid transfer pump comprising the flexible dome.

10. The implantable, biocompatible system in accordance with claim 9 wherein the confined flow passageway is connected to the flexible dome.

11. The implantable, biocompatible system in accordance with claim 10 wherein the second opposed plate comprises peripheral apertures configured to secure the hollow accumulation chamber to the patient.

12. The implantable, biocompatible system in accordance with claim 5 further comprising an aperture in the second opposed plate, the confined flow passageway extending into the aperture.

13. The implantable, biocompatible system in accordance with claim 12 wherein the liquid transfer pump is spaced apart from the hollow accumulation chamber, the confined flow passageway connected to the liquid transfer pump.

14. The implantable, biocompatible system in accordance with claim 13 wherein the second opposed plate comprises peripheral apertures configured to secure the hollow accumulation chamber to the patient.

15. The implantable, biocompatible system in accordance with claim 1 wherein the plurality of posts are made of rubber.

16. The implantable, biocompatible system in accordance with claim 1 wherein the plurality of posts are made of metal.

17. The implantable, biocompatible system in accordance with claim 1 wherein the plurality of posts comprise mesh.

18. The implantable, biocompatible system in accordance with claim 1 wherein the plurality of posts comprise screens.

* * * * *